United States Patent
Kutsuma

(10) Patent No.: US 11,298,011 B2
(45) Date of Patent: Apr. 12, 2022

(54) PROCESSING DEVICE, SETTING METHOD AND COMPUTER-READABLE RECORDING MEDIUM

(71) Applicant: OLYMPUS CORPORATION, Tokyo (JP)

(72) Inventor: Yuji Kutsuma, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 691 days.

(21) Appl. No.: 16/194,464

(22) Filed: Nov. 19, 2018

(65) Prior Publication Data
US 2019/0082942 A1 Mar. 21, 2019

Related U.S. Application Data

(63) Continuation of application No. PCT/JP2017/007659, filed on Feb. 28, 2017.

(30) Foreign Application Priority Data

May 30, 2016 (JP) .............................. JP2016-107825

(51) Int. Cl.
*A61B 1/045* (2006.01)
*A61B 1/00* (2006.01)
(Continued)

(52) U.S. Cl.
CPC ................ *A61B 1/045* (2013.01); *A61B 1/00* (2013.01); *A61B 1/00006* (2013.01);
(Continued)

(58) Field of Classification Search
CPC ....... A61B 1/045; A61B 1/00; A61B 1/00006; G02B 23/24; H04N 5/23245; H04N 5/2354; H04N 2005/2255
See application file for complete search history.

(56) References Cited

U.S. PATENT DOCUMENTS 9,326,664 B2   5/2016 Takei et al.
9,782,059 B2  10/2017 Saito et al.
(Continued)

FOREIGN PATENT DOCUMENTS

| GN | 104717917 A | 6/2015 |
| JP | 2010-142288 A | 7/2010 |
| WO | WO 2016/076314 A1 | 5/2016 |

OTHER PUBLICATIONS

Chinese Office Action dated Aug. 25, 2020 in Chinese Patent Application No. 201780033001.8.
(Continued)

*Primary Examiner* — Timothy J Neal
*Assistant Examiner* — Genja M Frankert
(74) *Attorney, Agent, or Firm* — Scully, Scott, Murphy & Presser, P.C.

(57) ABSTRACT

A processing device to which an endoscope inserted into a subject is connected includes: an image processor configured to execute image processing based on a setting value set in advance relating to the image processing on image data; a recorder configured to record setting information as setting values for respective multiple sets of image processing, the setting values being determined according to a combination of: at least one of identification information and observation light information; and each of multiple modes; an acquisition unit configured to acquire: at least one of the identification information and the observation light information; and information about one of the multiple modes selected by a user; and a setting unit configured to set the setting information specified based on a result of acquisition as the setting values used in the image processing.

4 Claims, 5 Drawing Sheets

| IMAGE PROCESSING MODE FOR SPECIAL LIGHT 2 (DRI) | MODE 1 | MODE 2 | MODE 3 |
|---|---|---|---|
| COLOR MODE | TREATMENT MODE | TREATMENT MODE | DIAGNOSIS MODE |
| BLOOD-VESSEL ENHANCEMENT | OFF | MILD | STRONG |
| STRUCTURE ENHANCEMENT | A2 | A3 | A1 |

T10

(51) Int. Cl.
*G02B 23/24* (2006.01)
*H04N 5/232* (2006.01)
*H04N 5/235* (2006.01)
*H04N 5/225* (2006.01)

(52) U.S. Cl.
CPC .......... *G02B 23/24* (2013.01); *H04N 5/2354* (2013.01); *H04N 5/23245* (2013.01); *H04N 2005/2255* (2013.01)

(56) References Cited

U.S. PATENT DOCUMENTS

| | | | |
|---|---|---|---|
| 2007/0088193 A1* | 4/2007 | Omori | A61B 1/0669 600/101 |
| 2010/0331624 A1* | 12/2010 | Suzuki | A61B 1/043 600/109 |
| 2012/0065469 A1* | 3/2012 | Allyn | A61B 1/005 600/109 |
| 2013/0278739 A1 | 10/2013 | Tanaka et al. | |
| 2015/0022647 A1 | 1/2015 | Takei et al. | |
| 2015/0092032 A1* | 4/2015 | Kuramoto | G02B 23/2469 348/68 |
| 2016/0095508 A1* | 4/2016 | Terliuc | A61B 1/00082 134/18 |
| 2018/0214009 A1* | 8/2018 | Endo | A61B 1/00059 |
| 2019/0082929 A1* | 3/2019 | Watanabe | A61B 1/00006 |

OTHER PUBLICATIONS

International Search Report dated May 30, 2017 issued in PCT/JP2017/007659.

\* cited by examiner

FIG.3A

|  | WHITE LIGHT | SPECIAL LIGHT 1 (NBI) | SPECIAL LIGHT 2 (DRI) |
|---|---|---|---|
| UPPER SCOPE | SETTING INFORMATION 1 | SETTING INFORMATION 2 | SETTING INFORMATION 3 |
| LOWER SCOPE | SETTING INFORMATION 4 | SETTING INFORMATION 5 | SETTING INFORMATION 6 |
| TRANSNASAL SCOPE | SETTING INFORMATION 7 | SETTING INFORMATION 8 | SETTING INFORMATION 9 |

FIG.3B

|  | WHITE LIGHT | SPECIAL LIGHT 1 (NBI) | SPECIAL LIGHT 2 (DRI) |
|---|---|---|---|
| UPPER SCOPE | SETTING INFORMATION 1 | SETTING INFORMATION 2 | SETTING INFORMATION 3 |
| LOWER SCOPE | SETTING INFORMATION 1 | SETTING INFORMATION 2 | SETTING INFORMATION 3 |
| TRANSNASAL SCOPE | SETTING INFORMATION 1 | SETTING INFORMATION 2 | SETTING INFORMATION 3 |

FIG.3C

|  | WHITE LIGHT | SPECIAL LIGHT 1 (NBI) | SPECIAL LIGHT 2 (DRI) |
|---|---|---|---|
| UPPER SCOPE | SETTING INFORMATION 1 | SETTING INFORMATION 1 | SETTING INFORMATION 1 |
| LOWER SCOPE | SETTING INFORMATION 4 | SETTING INFORMATION 4 | SETTING INFORMATION 4 |
| TRANSNASAL SCOPE | SETTING INFORMATION 7 | SETTING INFORMATION 7 | SETTING INFORMATION 7 |

FIG.4

| IMAGE PROCESSING MODE FOR SPECIAL LIGHT 2 (DRI) | MODE 1 | MODE 2 | MODE 3 |
|---|---|---|---|
| COLOR MODE | TREATMENT MODE | TREATMENT MODE | DIAGNOSIS MODE |
| BLOOD-VESSEL ENHANCEMENT | OFF | MILD | STRONG |
| STRUCTURE ENHANCEMENT | A2 | A3 | A1 |

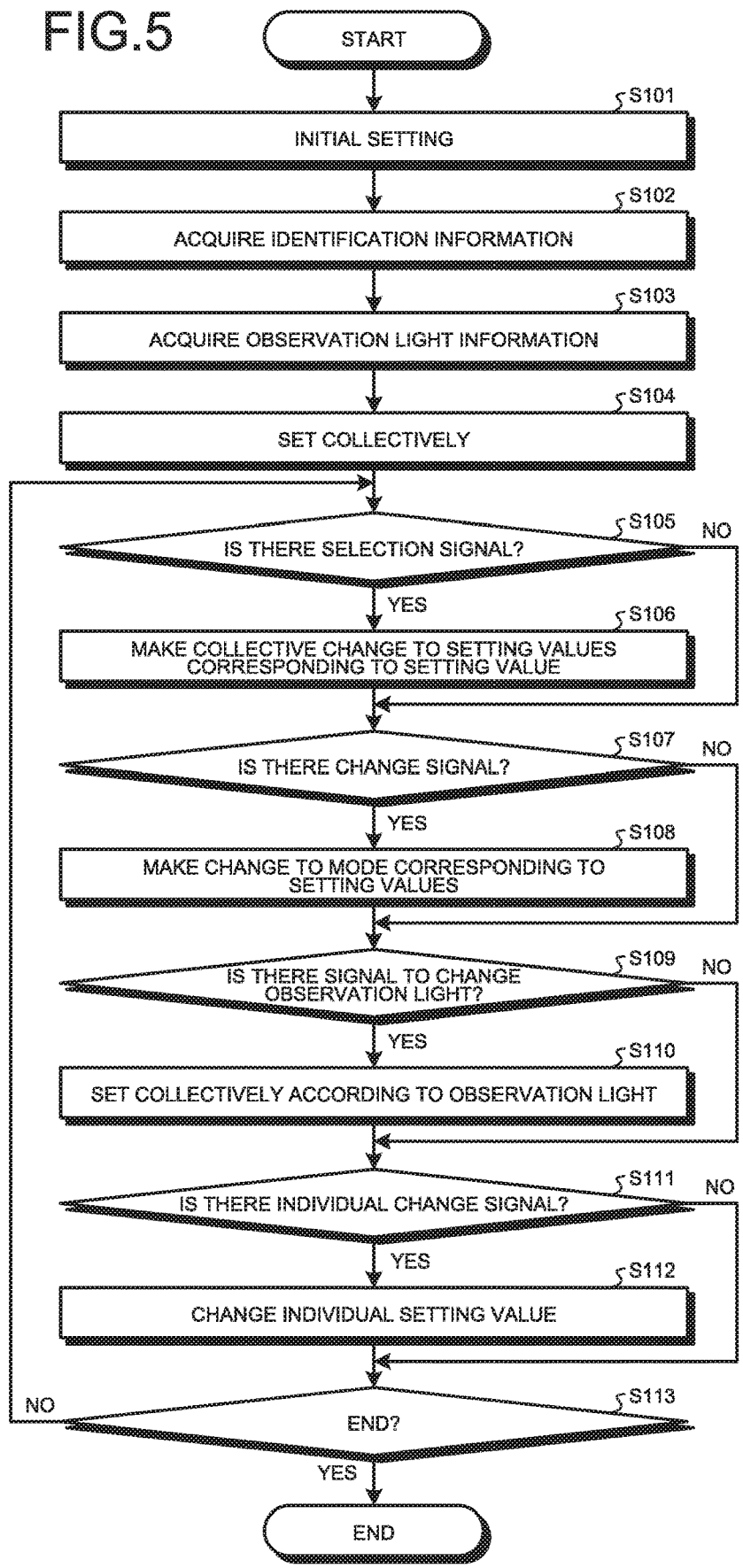

_US 11,298,011 B2_

PROCESSING DEVICE, SETTING METHOD AND COMPUTER-READABLE RECORDING MEDIUM

CROSS-REFERENCE TO RELATED APPLICATION

This application is a continuation of PCT international application Ser. No. PCT/JP2017/007659 filed on Feb. 28, 2017 which designates the United States, incorporated herein by reference, and which claims the benefit of priority from Japanese Patent Applications No. 2016-107825, filed on May 30, 2016, incorporated herein by reference.

BACKGROUND

The present disclosure relates to a processing device, a setting method and a computer-readable recording medium.

In the related art, a technique for changing setting values for respective multiple sets of image processing that are executed by an image processor in order to obtain preferable observation images in a processing device (processor) to which an endoscope is connected has been known (see Japanese Laid-open Patent Publication No. 2010-142288). This technique automatically changes the setting values for the respective multiple sets of image processing that are executed by the image processor according to the temperature of an imaging device that is provided at the tip part of the endoscope.

SUMMARY

According to one aspect of the present disclosure, there is provided a processing device to which an endoscope inserted into a subject is connected, the processing device including: an image processor configured to execute image processing based on a setting value set in advance relating to the image processing on image data generated by the endoscope by capturing an image of an inside of the subject; a recorder configured to record setting information as setting values for respective multiple sets of image processing, the setting values being determined according to a combination of: at least one of identification information for identifying a type of the endoscope and observation light information about observation light that is emittable by a light source device that supplies the observation light to the endoscope for irradiating the inside of the subject; each of multiple modes; and an acquisition unit configured to acquire: at least one of the identification information for identifying the endoscope connected to the processing device and the observation light information supplied by the light source device; and information about one of the multiple modes selected by a user; and a setting unit configured to set the setting information specified based on a result of acquisition by the acquisition unit as the setting values used in the image processing executed by the image processor.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 3A is a diagram illustrating exemplary combination information that a setting information recorder of a processing device according to the embodiment records;

FIG. 3B is a diagram illustrating other exemplary combination information that the setting information recorder of the processing device according to the embodiment records;

FIG. 3C is a diagram illustrating other exemplary combination information that the setting information recorder of the processing device according to the embodiment records;

FIG. 4 is a diagram illustrating exemplary setting information that the setting information recorder of the processing device according to the embodiment records; and FIG. 5 is a flowchart illustrating an overview of a process that the processing device according to the embodiment executes.

DETAILED DESCRIPTION

An embodiment for carrying out the present disclosure ("embodiment" below) will be described. The embodiment will be described by exemplifying a medical endoscope system that captures in-vivo image data of the body cavity of a subject, such as a patient, and displays the image data. The following embodiment does not limit the disclosure. Furthermore, in description of drawings, the same components are denoted with the same reference number and descried.

Configuration of Endoscope System

Figure 1:
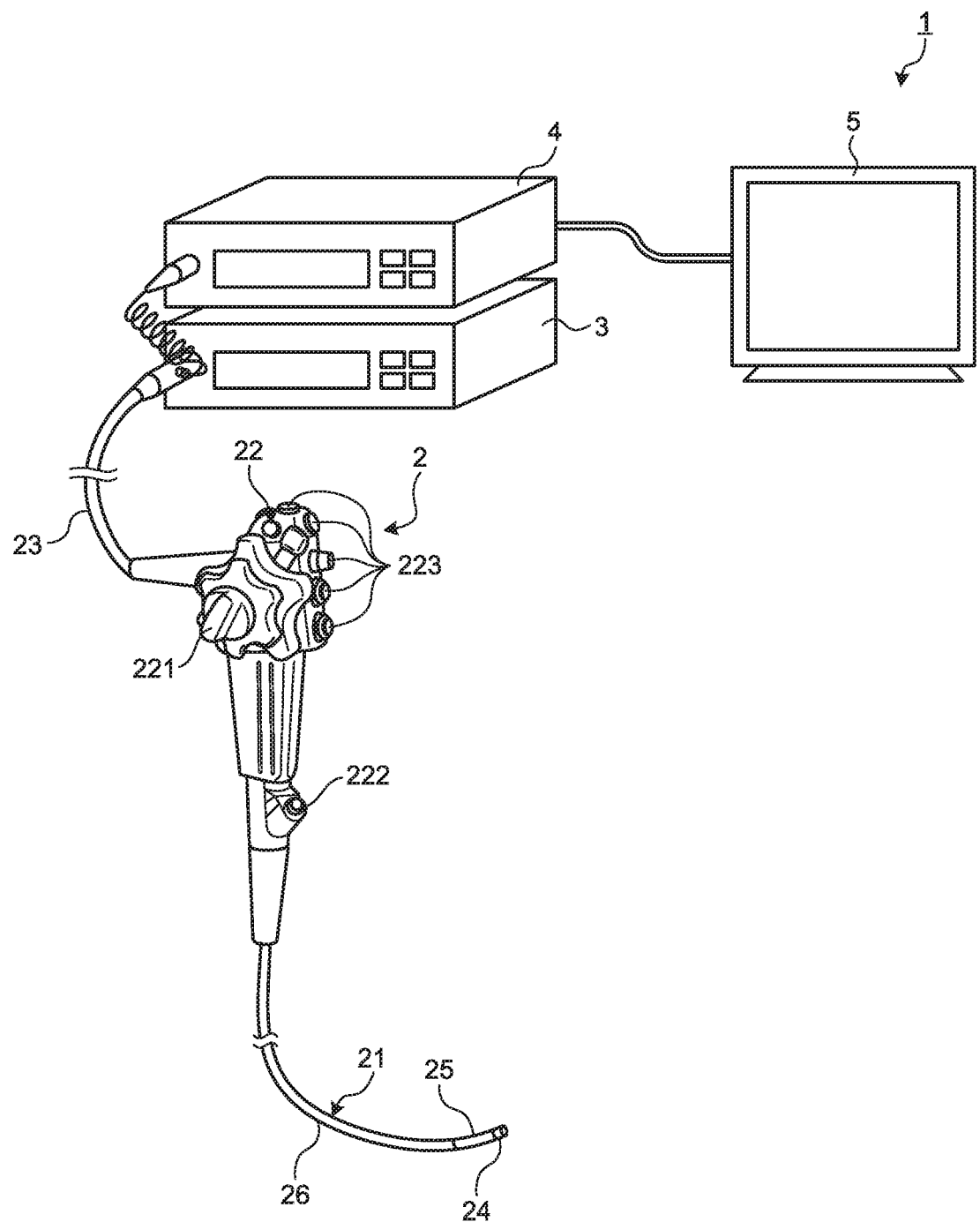
FIG. 1 is a diagram illustrating a schematic configuration of an endoscope system according to an embodiment.
Figure 2:
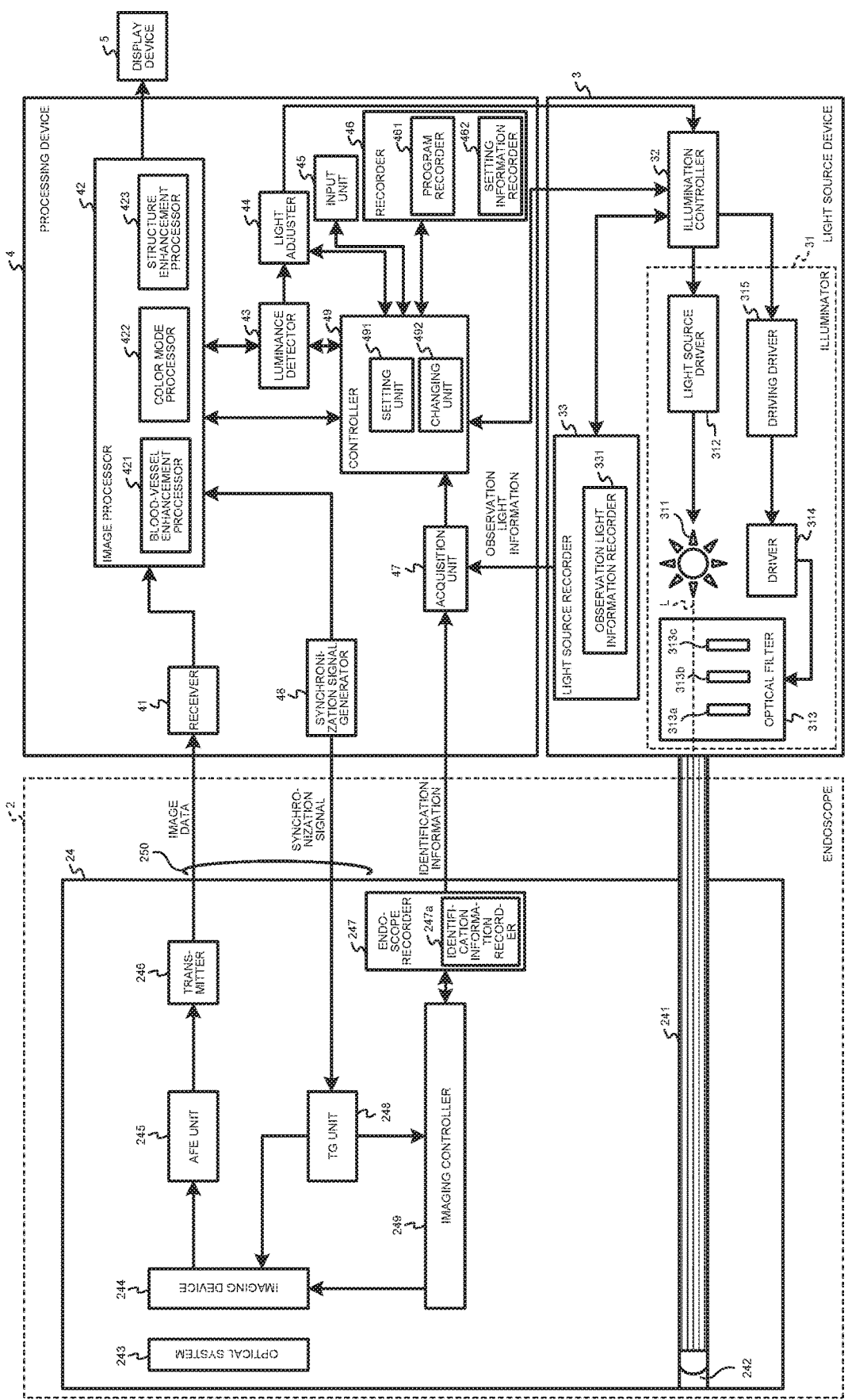
FIG. 2 is a block diagram illustrating a functional configuration of a relevant part of the endoscope system according to the embodiment.

FIG. 1 is a diagram illustrating a schematic configuration of an endoscope system according to an embodiment. FIG. 2 is a block diagram illustrating a functional configuration of a relevant part of the endoscope system according to the embodiment.

An endoscope system 1 illustrated in FIGS. 1 and 2 includes an endoscope 2 (endoscope scope) that inserts its tip part into the body cavity of the subject, thereby capturing image data of a subject; a light source device 3 that generates illumination light that is emitted from the tip of the endoscope 2; a processing device 4 that performs given image processing on the image data that is captured by the endoscope 2 and overall controls entire operations of the endoscope system 1; and a display device 5 that displays an observation image (in-vivo image) corresponding to image data on which the image processing is performed by the processing device 4. The embodiment will be described by exemplifying a soft endoscope as the endoscope 2, but any one of a 3D endoscope, a hard endoscope and a transnasal endoscope may be used.

Configuration of Endoscope

A configuration of the endoscope 2 will be described.

The endoscope 2 includes an insertion unit 21 that is flexible an elongated; an operation unit 22 that is connected to a base end side of the insertion unit 21 and that receives inputs of various operation signals; and a universal cord 23 that extends in a direction different from a direction in which the insertion unit 21 extends from the operation unit 22 and that incorporates various cables that are connected to the light source device 3 and the processing device 4.

The insertion unit 21 includes a tip part 24 that incorporates an imaging device 244 that is formed by two-dimensionally arranging pixels that receive light and perform photoelectric conversion to generate electric signals (image signals); a curving part 25 that consists of multiple curving pieces and that can be curved flexibly; and a flexible pipe 26 that is connected to a base end side of the curving part 25 and that is flexible and elongated.

The tip part 24 includes a light guide 241, an illumination lens 242, an optical system 243, the imaging device 244, an analog front end 245 ("AFE unit 245" below), a transmitter 246, an endoscope recorder 247, a timing generator unit 248 ("TG unit 248" below) and an imaging controller 249.

The light guide 241 consists of glass fibers, etc., and forms a light guide path for light that is emitted by the light source device 3. The illumination lens 242 is provided at the tip of the light guide 241 and diffuses the light that is guided by the light guide 241 to an object.

The optical system 243 consists of one or more lenses, a prism, etc., and has an optical zoom function to change the angle of view and a focus function to change the focal point.

The imaging device 244 performs photoelectric conversion on light from the optical system 243 and generates electric signals as image data. The imaging device 244 consists of an imaging sensor, such as a charge coupled device (CCD) or a complementary metal oxide semiconductor (CMOS). The imaging device 244 is provided in an imaging position in which the optical system 243 forms an object image. Under the control of the imaging controller 249, the imaging device 244 generates image data according to a signal that is input from the TG unit 248.

The AFE unit 245 reduces noise components that are contained in the image data that is input from the imaging device 244, and performs correlated double sampling (CDS) processing to adjust the amplification factor of the image signal and maintain a given output level and A/D conversion processing to perform A/D conversion on the image data and outputs the processed image data to the transmitter 246.

The transmitter 246 transmits digital image data that is input from the AFE unit 245 to the processing device 4. The transmitter 246, for example, performs parallel/serial conversion processing to convert parallel-signal image data to serial-signal image data or E/O conversion processing to convert electric-signal image data into optical-signal image data and transmits the processed image data to the processing device 4.

The endoscope recorder 247 records various types of information on the endoscope 2. The endoscope recorder 247 includes an identification information recorder 247a that records identification information that identifies the endoscope 2. The identification information includes an endoscope ID for identifying the endoscope 2, a model year of the endoscope 2, type information representing the type of the endoscope 2, a specification information of the endoscope 2, a method of transmission of the image data performed by the endoscope 2, a rate of transmission of image data performed by the endoscope 2, information on observation light of the light source device 3 corresponding to the endoscope 2 and information of a type of the processing device 4 that the endoscope 2 is able to deal with. The endoscope recorder 247, for example, is realized by using a read only memory (ROM), a flash memory, etc.

The TG unit 248 generates pulses for various types of signal processing to drive the imaging device 244 and the imaging controller 249, respectively. The TG unit 248 outputs the pulse signals to the imaging device 244 and the imaging controller 249.

The imaging controller 249 controls imaging performed by the imaging device 244. The imaging controller 249 consists of a central processing unit (CPU), a register that records various programs, etc.

The operation unit 22 includes a curving knob 221 that causes the curving part 25 in top-down and left-right directions; a processing tool insertion unit 222 that inserts a processing tool, such as biological forceps, an electric scalpel or an examination probe, into the body cavity of the subject; and multiple switches 223 serving as an operation input unit that inputs operation instruction signals to, in addition to the processing device 4 and the light source device 3, peripherals, such as an insufflation unit, a water delivery unit and screen display control unit. The processing tool that is inserted from the processing tool insertion unit 222 rises from an opening (not illustrated in the drawings) via a processing tool channel of the tip part 24 (not illustrated).

The universal cord 23 incorporates at least the light guide 241 and one or multiple assembled cables 250 each of which is an assembly of signal lines. The assembled cable 250 includes at least a signal line to transmit a synchronization signal that is output from the processing device 4 to be described below and a signal line to transmit image data.

Configuration of Light Source Device

A configuration of the light source device 3 will be described.

The light source device 3 includes an illuminator 31, an illumination controller 32 and a light source recorder 33.

Under the control of the illumination controller 32, the illuminator 31 sequentially switch and emits multiple illumination lights with wavelength bands different from one another to the object (subject). The illuminator 31 includes a light source unit 311, a light source driver 312, an optical filter 313, a driver 314 and a driving driver 315.

The light source unit 311 consists of a white LED and one or more lenses and emits white light to the optical filter 313 under the control of the light source driver 312. The white light that is generated by the light source unit 311 is emitted from the tip of the tip part 24 to the object via the optical filter 313 and the light guide 241. The light source unit 311 may consist of a red LED, a green LED and a blue LED and, with a current supplied by the light source driver 312 to each of the LEDs, emit red light, green light and blue light sequentially. Alternatively, the light source unit 311 may emit lights simultaneously from the white lED, the red LED, the green LED and the blue LED or emit white light to the subject with an electric-discharge lamp, such as a xenon lamp, to acquire images.

Under the control of the illumination controller 32, the light source driver 312 supplies an electronic current to the light source unit 311 to cause the light source unit 311 to emit white light.

The optical filter 313 consists of multiple filters that transmit only light with a given wavelength band. Under the control of the driver 314, a given filter of the optical filter 313 is arranged on an optical path L of white light that is emitted by the light source unit 311 such that the filter can be inserted and ejected. The optical filter 313 has a transmission characteristic that limits white light that is emitted from the light source unit 311 to a given wavelength band. The driver 314 causes the optical filter 313 to be arranged on the optical path L of white light that is emitted by the light source unit 311 such that the optical filter 313 can be inserted and extracted.

A filter 313a sequentially transmits lights with respective wavelength bands of red light (R), green light (G) and blue light (B) (for example, red: 600 nm to 700 nm, green: 500 nm to 600 nm, and blue: 400 nm to 500 nm). When the endoscope system 1 performs white light observation (WLI), the driver 314 causes the filter 313a to be arranged on the white-light optical path L and rotated so that, according to the wavelength bands of red, green and blue, the white light (W illumination) that is emitted by the light source unit 311 enables sequential emission of any one of red light (R illumination), green light (G illumination) and blue light (B illumination) with narrowed bands to the endoscope 2 (frame sequential method).

A filter 313b transmits each of narrowband blue light (for example, 390 nm to 445 nm) and narrowband green light (for example, 530 nm to 550 nm). Specifically, when the endoscope system 1 performs narrowband light observation (NBI: Narrow Band Imaging) as special light observation, the driver 314 causes the filter 313b to be arranged on the light path L of white light.

A filter 313c transmits each of two narrowband red lights (for example, 600 nm and 630 nm). Specifically, when the endoscope system 1 performs narrowband light observation (DBI: Dual Red Imaging) as special light observation, the driver 314 causes the filter 313c to be arranged on the light path L of white light.

The optical filter 313 may be provided with, when the endoscope system 1 performs fluorescence observation (AFI: Auto Fluorescence Imaging) as special light observation, a filter, for white light that is emitted from the light source unit 311, that transmits each of excitation light (for example, 390 nm to 470 nm) for observing autofluorescence from a fluorescent substance, such as collagen, and light with a wavelength (for example, 540 nm to 560 nm) that is absorbed into hemoglobin in blood and, when the endoscope system 1 performs infrared light observation (IRI: Infra Red Imaging) as special light observation, a filter that transmits each of two infrared lights (for example, 790 nm to 8200 nm and 905 nm to 870 nm).

The driver 314 consists of a stepping motor, a DC motor, etc., and, under the control of the driving driver 315, arranges each of the filters of which the optical filter 313 consists on the optical path L of white light.

The driving driver 315 supplies a given electric current to the driver 314 under the control of the illumination controller 32.

The illumination controller 32 causes the light source unit 311 to emit white light at a given cycle according to an instruction signal that is input from the processing device 4.

The light source recorder 33 records various types of information on the light source device 3. The light source recorder 33 includes an observation light information recorder 331 that records observation light information on observation light that the light source device 3 is able to emit.

Configuration of Processing Device

A configuration of the processing device 4 will be described.

The processing device 4 includes a receiver 41, an image processor 42, a luminance detector 43, a light adjuster 44, an input unit 45, a recorder 46, an acquisition unit 47, a synchronization signal generator 48 and a controller 49.

The receiver 41 receives the image data that is transmitted from the transmitter 246 and outputs the image data to the image processor 42. When the image data that is transmitted from the transmitter 246 is a parallel signal, the receiver 41 performs parallel/serial conversion processing to perform conversion into a serial signal and outputs the image data to the image processor 42 and, when the image data that is transmitted from the transmitter 246 is an optical signal, the receiver 41 performs O/E conversion processing to perform conversion into an electric signal and outputs the image data to the image processor 42.

The image processor 42 is realized using a FPGA or the like. Under the control of the controller 49, the image processor 42 generates an in-vivo image for the display device 5 to display based on the image data that is input from the receiver 41 and outputs the in-vivo image to the display device 5. The image processor 42 performs given image processing on the image data to generate an in-vivo image. The image processing herein includes synchronization processing, optical black reduction processing, white balance adjustment processing, color matrix arithmetic processing, gamma correction processing, color reproduction processing, edge enhancement processing and format conversion processing. Furthermore, the image processor 42 includes at least a blood-vessel enhancement processor 421, a color mode processor 422 and a structure enhancement processor 423.

Under the control of the controller 49, the blood-vessel enhancement processor 421 executes blood-vessel enhancement processing to enhance blood vessels by changing the tone on the image data. For example, the blood-vessel enhancement processor 421 executes color conversion processing to convert the hue and chroma on the image data and executes blood-vessel enhancement processing on the image data by performing color adjustment to change the color balance and tone curve.

Under the control of the controller 49, the color mode processor 422 executes, on the image data, color mode processing to change the resolution to a resolution suitable for diagnosis of the observation image.

Under the control of the controller 49, the structure enhancement processor 423 executes, on the image data, structure enhancement processing to enhance the structure by changing the edge and contrast and changing the intensity of noise reduction.

The luminance detector 43 detects a luminance level corresponding to each image based on RGB image information that is contained in the image data that is input from the image processor 42, records the detected brightness level in a memory that is provided inside, and outputs the brightness level to each of the light adjuster 44 and the controller 49.

Under the control of the controller 49, the light adjuster 44 sets a light emission condition, such as an amount of light that the light source device 3 generates and light emission timing, and outputs a light adjustment signal containing the set light emission condition to the light source device 3.

The input unit 45 receives inputs of various signals, such as operation instruction signals to instruct the endoscope system 1 to perform operations. The input unit 45 consists of switches, etc. The input unit 45 receives an input of an instruction signal to change any one of multiple modes and setting values for respective multiple sets of image processing.

The recorder 46 is realized by using a read only memory (ROM) and records various programs for causing the endoscope system 1 to operate, data containing various parameters necessary for the endoscope system 1 to operate, etc. The recorder 46 includes a program recorder 461 and a setting information recorder 462.

The program recorder 461 records various programs for causing the endoscope system 1 to operate and a program according to the embodiment.

The setting information recorder 462 records setting information in which setting values for the respective multiple sets of image processing that the image processor 42 executes are determined according to a combination of identification information and observation light information and each of the multiple modes. The setting information recorder 462 records combination information with which setting information that is determined by the combination of identification information and observation light information is associated.

FIG. 3A is a schematic diagram illustrating exemplary setting information that the setting information recorder 462 records and is a schematic diagram illustrating exemplary setting information that is determined by the combination of identification information and observation light information. In combination information T1 represented in FIG. 3A, setting information that is determined by combinations of multiple sets of identification information and multiple sets of setting information is associated. Specifically, in the combination information T1, setting information that is determined by a combination of a type of the endoscope 2 and a type of observation light that the light source device 3 emits is associated. For example, in the combination information T1, when the observation light is "special light 2 (for example, DRI)" in the case where the identification information is "an upper scope", "setting information 3" is associated.

FIG. 3B is a schematic diagram illustrating other exemplary setting information that the setting information recorder 462 records and is a schematic diagram illustrating exemplary setting information that is determined by observation light information. In the combination information T2 illustrated in FIG. 3B, setting information that is determined by multiple sets of observation light information is associated regardless of the type of the endoscope 2. Specifically, in the combination information T2, setting information that is determined by the type of observation light that the light source device 3 emits is associated. For example, in the combination information T2, when the observation light is "special light 2 (for example, DRI)", "setting information 3" is associated regardless of the type of the endoscope 2.

FIG. 3C is a schematic diagram illustrating exemplary other setting information that the setting information recorder 462 records and is a schematic diagram illustrating exemplary setting information that is determined by identification information. In the combination information T3 represented in FIG. 3C, setting information that is determined by multiple sets of identification information is associated regardless of observation light. Specifically, in the combination information T3, setting information that is determined by the type of the endoscope 2 is associated. For example, in the combination information T3, when the identification information is "upper scope", "setting information 1" is associated regardless of the observation light.

FIG. 4 is a schematic diagram illustrating setting information that the setting information recorder 462 records. FIG. 4 illustrates details of the above-described "setting information 3" in FIG. 3.

In the setting information T10 represented in FIG. 4, setting values (setting levels) for multiple sets of image processing are determined for each of the multiple modes so as not to lose medical utility due to deterioration of image quality. Specifically, in the setting information T10, in the case of Mode 1, a setting value for the color mode processing that is performed by the color mode processor 422 is written in a treatment mode setting value, a setting value for the blood-vessel enhancement processing that is performed by the blood-vessel enhancement processor 421 is written in an off setting value, and a setting value for the structure enhancement processing that is performed by the structure enhancement processor 423 is written in an A2 setting value. As described above, the setting information recorder 462 records the setting information in which the setting values for the respective multiple image processing are determined according to the combination of the identification information of the endoscope 2 connected to the processing device 4 and the observation light information on the light source device 3 and each of the multiple modes. In other words, in the setting information recorder 462, the multiple modes to which the setting values for the respective multiple sets of image processing are assigned are recorded in association with each combination of identification information of the endoscope 2 and observation light information on the light source device 3. Not only one setting value but a given range (width) or multiple values may be set as long as medical usability is not lost due to image quality deterioration. Furthermore, setting values are set by a manufacturer, a customer or the like in advance. Furthermore, the number of mode may be changed as appropriate.

FIG. 1 and FIG. 2 will be referred back to continue describing the configuration of the endoscope 2.

The acquisition unit 47 acquires identification information that identifies the endoscope 2 from the identification information recorder 247a of the endoscope 2 and acquires at least one set of observation light information from the observation light information recorder 331 of the light source device 3 and outputs the identification information and the observation light information to the controller 49.

The synchronization signal generator 48 generates a synchronization signal containing at least a vertical synchronization signal and outputs the synchronization signal to the TG unit 248 via the assembled cable 250 and outputs the synchronization signal to the image processor 42.

The controller 49 consists of a CPU, etc., and performs drive control on each component including the imaging device 244 and the light source device 3 and input/output control on information to each component. The controller 49 outputs setting data for imaging control that is recorded in the recorder 46, for example, the address information of an image to be read, to the imaging controller 249 via the assembled cable 250. The controller 49 includes a setting unit 491 and a changing unit 492.

The setting unit 491 sets setting values for the respective multiple sets of image processing in the image processor 42 based on at least one of the identification information and the observation light information that are acquired by the acquisition unit 47 and the setting information that the setting information recorder 462 records. Specifically, based on at last one of the identification information and the observation light information that are acquired by the acquisition unit 47 and the setting information that the setting information recorder 462 records, the setting unit 491 collectively sets a setting value according to the blood vessel enhancement processing performed by the blood-vessel enhancement processor 421, a setting value according to the color mode processing performed by the color mode processor 422, and a setting value according to the structure enhancement processing performed by the structure enhancement processor 423.

When the input unit 45 receives an input of an instruction signal to change any one of the setting values of the respective multiple sets of image processing, the changing unit 492 collectively changes the setting values of the respective multiple sets of image processing that are set by the setting unit 491 in the image processor 42 to setting values for the respective sets of image processing that are assigned to the mode of the setting value to which the setting value is changed according to the instruction signal and, meanwhile, when the input unit 45 receives an input of an instruction signal to make a change to any one of the multiple modes, the changing unit 492 makes a collective change to setting values of the respective sets of image processing that are assigned to the mode to which the mode is changed according to the instruction signal.

Process performed by Processing Device

A process that the processing device 4 executes will be described. FIG. 5 is a flowchart illustrating an overview of the process that the processing device 4 executes.

As illustrated in FIG. 5, first of all, as illustrated in FIG. 5, first of all, according to an operation performed by the manufacturer or a service person via the input unit 45, the setting unit 491 makes an initial setting to generate setting information in which setting values (setting levels) for respective multiple sets of image processing executable by the image processor 42 are assigned to each of multiple modes executable by a combination of the endoscope 2 and the light source device 3 that are connectable to the processing device 4 and record the setting information in the setting information recorder 462 (step S101). This processing may be omitted when the initial setting is made by the manufacturer before shipment of the processing device 4. Needless to say, the initial setting may be made by a service person or a customer after shipment of the processing device 4.

Subsequently, the acquisition unit 47 acquires identification information from the endoscope 2 that is connected to the processing device 4 (step S102) and acquires observation light information from the light source device 3 that is connected to the processing device 4 (step S103). It suffices if the acquisition unit 47 is able to acquire at least one of the identification information and the observation light information.

Thereafter, based on the identification information and the observation light information that are acquired by the acquisition unit 47 and the setting information that the setting information recorder 462 records, the setting unit 491 collectively sets, in the image processor 42, setting values for the respective sets of multiple image processing in the multiple modes executable by the endoscope 2 and the light source device 3 that are connected to the processing device 4 (step S104). Accordingly, the image processor 42 is able to perform, on image data that is input from the endoscope 2, image processing by appropriate image-processing setting values corresponding to the type of the endoscope 2 and the type of observation light that is emitted by the light source device 3. As a result, it is possible to enable high convenience to users and prevention of image quality of observation images from deteriorating. Needless to say, the setting unit 491 may collectively set, in the image processor 42, setting values for the respective multiple sets of image processing in the multiple modes that are executable by the endoscope 2 and the light source device 3, which are connected to the processing device 4, based on at least one of the identification information and the observation light information that are acquired by the acquisition unit 47 and the setting information that the setting information recorder 462 records. For example, the setting unit 491 may collectively set, in the image processor 42, setting values for the respective multiple sets of image processing in the multiple modes executable by the endoscope 2 and the light source device 3, which are connected to the image processing device 4, based on the identification information that is acquired by the acquisition unit 47 and the setting information that the setting information recorder 462 records, or may collectively set, in the image processor 42, setting values for the respective multiple sets of image processing in the multiple modes executable by the endoscope 2 and the light source device 3, which are connected to the image processing device 4, based on the observation light information that is acquired by the acquisition unit 47 and the setting information that the setting information recorder 462 records.

Subsequently, when a selection signal to select a mode is received from the input unit 45 (YES at step S105), the changing unit 492 makes a collective change to setting values of the respective sets of image processing corresponding to the mode that is selected according to the selection signal (step S106). For example, as illustrated in FIG. 4, when the user selects Mode 3 from Mode 1 via the input unit 45, the changing unit 492 sets the setting value for the blood-vessel enhancement processing performed by the blood-vessel enhancement processor 421 at a strong-mode setting value from an off-mode setting value and sets the color mode processing that is performed by the color mode processor 422 at a diagnosis-mode setting value from the treatment-mode setting value and, meanwhile, collectively changes the setting value for the structure enhancement processing that is performed by the structure enhancement processor 423 from the A2 setting value to an A1 setting value. Accordingly, selecting only a mode enables a collective change to setting values for the respective sets of image processing associated with the mode and thus the user is able to observe the subject with given image quality being secured without performing complicated operations and accordingly improve diagnosis of or treatment on the subject. After step S106, the processing device 4 moves to step S107, which will be described below.

At step S105, when no selection signal to select a mode is received from the input unit 45 (NO at step S105), the processing device 4 moves to step S107, which will be described below.

At step S107, when a change signal to change a setting value for any one of the multiple sets of image processing is received from the input unit 45 (YES at step S107), the changing unit 492 makes a change to a mode corresponding to the setting value that is selected according to the change signal (step S108). For example, as illustrated in FIG. 4, when the user changes the setting value for the blood-vessel enhancement processing from the strong-mode setting value to the off-mode setting value via the input unit 45, the changing unit 492 changes the mode of the image processor 42 from Mode 3 to Mode 1, changes the setting value for the color mode processing performed by the color mode processor 422 from the diagnosis-mode setting value to the treatment-mode setting value, and collectively changes the setting value for the structure enhancement processing performed by the structure enhancement processor 423 from the A1 setting value to the A2 setting value. Accordingly, the user only changes a setting value for image processing to implement an automatic change to a mode corresponding to the setting value and implement a collective change to setting values for the respective sets of image processing associated with the mode and thus is able to observe the subject with the given image quality being secured without performing complicated operations and improve diagnosis of and treatment on the subject. After step S108, the processing device 4 moves to step S109, which will be described below.

At step S107, when no change signal to change a setting value for any one of the multiple sets of image processing is received from the input unit 45 (NO at step S107), the processing device 4 moves to step S109, which will be described below.

At step S109, when a signal to change the observation light is received from the input unit 45 (YES at S109), the changing unit 492 makes a collective setting corresponding to the observation light (step S110). For example, as illustrated in FIGS. 3A to 3C, when the user switches the observation light to white light via the input unit 45, the changing unit 492 changes the setting values for the respective multiple sets of image processing that the image processor 42 is caused to execute from "setting information 2" to "setting information 1". Accordingly, only switching the observation light that the light source device 3 emits enables an automatic collective change to setting values associated with the observation light and thus the user is bale to observe the subject with the given image quality being secured without performing complicated operations and accordingly improve diagnosis of and treatment on the subject. After step S110, the processing device 4 moves to step S111, which will be described below.

At step S109, when no signal to change the observation light is received from the input unit (NO at step S109), the processing device 4 moves to step S111, which will be described below.

At step S111, when an individual change signal to change setting values for sets of image processing that are changeable individually is received from the input unit 45 (YES at S111), the changing unit 492 changes the setting values for the image processing the can be set individually to setting values corresponding to the individual change signal regardless of the mode in the image processor 42 (step S112). Specifically, the changing unit 492 changes the setting values in the image processor 42, i.e., the setting values for sets of image processing, such as noise reduction processing and auto gain control processing ("AGC processing" below), other than the sets of image processing (for example, the blood-vessel enhancement processing, the color mode processing and the structure enhancement processing) that are chosen in the image processing to make a collective setting in the initial setting at step S101, to setting values according to the individual change signal. After step S112, the processing device 4 moves to step S113 to be described below.

At step S111, when no individual change signal to change setting values for sets of image processing that are changeable individually is received from the input unit 45 (NO at step S111), the processing device 4 moves to step S113 to be described below.

At step S113, when an end signal of an instruction to end is received from the input unit 45 (YES at step S113), the processing device 4 ends the process. On the other hand, when no end signal of an instruction to end is received from the input unit 45 (NO at step S113), the processing device 4 returns to step S105 described above.

According to the above-described embodiment, the setting unit 491 sets setting values for the respective multiple sets of image processing that the image processor 42 is caused to execute based on at least one of the identification information and the observation light information, which are acquired by the acquisition unit 47, and the setting information that the setting information recorder 462 records and this enables high convenience to users and prevention of image quality of observation images from deteriorating.

According to an embodiment, when an instruction signal to change any one of setting values for multiple sets of image-processing is received from the input unit 45, the changing unit 492 collectively changes the setting values for the respective sets of processing that are determined by a mode corresponding to a setting value to which the setting value is changed according to the instruction signal and, meanwhile, when an instruction signal to make a change to any one of the multiple modes is received from the input unit 45, the changing unit 492 collectively changes setting values for respective sets of image processing that are determined by the mode to which the mode is changed according to the instruction signal and thus it is possible to prevent image quality of observation images from deteriorating.

According to an embodiment, a setting value of each of the multiple sets of image processing, which are set by the setting unit 491, cannot be changed alone and thus medical utility of observation images can be maintained.

Other Embodiment

In the embodiment, image data is transmitted to the processing device via the transmission cable; however, transmission need not be wired and may be wireless. In this case, it suffices if image data, etc., be transmitted to the processing device according to given wireless communication standards (for example, Wi-Fi (trademark) or Bluetooth (trademark)). Needless to say, wireless communication may be performed according to other wireless communication standards.

In the embodiment, the processing device and the light source device are different components; however, they are not limited thereto and, for example, the processing device and the light source device may be formed integrally.

The embodiment has been described by exemplifying the sequential lighting endoscope, and a simultaneous lighting endoscope may be also used.

In the embodiment, the endoscope is inserted into the subject and, for example, even a capsule endoscope or an imaging device that captures images of a subject may be used.

In the description of the flowchart herein, expressions such as, "first of all", "thereafter", "subsequently", etc., are used to clearly represent the anteroposterior relation of each process; however, the order of a process necessary to carry out the present disclosure is not determined uniquely by those expressions. In other words, the order of the process in the flowchart described herein can be changed within a scope without inconsistency.

As described above, the present disclosure can include various embodiments not described herein and it is possible to make various design changes within the scope of the technical idea that is specified by the claims.

The present disclosure has an effect that high usability to users and prevention of image quality of observation images from deteriorating are enabled.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A processing device to which an endoscope insertable into a subject is connected, the processing device comprising:
    an image processor configured to execute image processing based on a setting value set in advance relating to the image processing on image data generated by the endoscope by capturing an image of an inside of the subject; and
    a controller configured to:
        access a recorder configured to record setting information as setting values for respective multiple sets of image processing, the setting values being determined according to a combination of:
at least one of identification information for identifying a type of the endoscope and observation light information about observation light that is emittable by a light source device that supplies the observation light to the endoscope for irradiating the inside of the subject; and
each of multiple modes,
wherein, for each combination of the identification information and the observation light information, the each of multiple modes is recorded in correspondence with the setting values for the respective multiple sets of image processing;
perform an acquisition of:
at least one of the identification information for identifying the endoscope connected to the processing device and the observation light information supplied by the light source device; and
information about one of the multiple modes selected by a user; and
set the setting information specified based on a result of the acquisition as the setting values used in the image processing executed by the image processor;
wherein the controller is further configured to:
receive an instruction signal to change any one of the multiple modes and the setting values for the respective multiple sets of the image processing; and
in response to receiving the instruction signal to change any one of the setting values for the multiple sets of the image processing, collectively change setting values for respective sets of image processing that are determined by a mode corresponding to a setting value to which the setting value is changed according to the instruction signal and, meanwhile, in response to receiving the instruction signal to make a change to any one of the multiple modes, collectively change setting values for respective sets of image processing that are determined by the mode into which the mode is changed according to the instruction signal.

2. The processing device according to claim 1, wherein the multiple modes at least correspond to steps in endoscopic surgery.

3. A setting method executed by a processing device to which an endoscope insertable into a subject is connected, the setting method comprising:
executing, by an image processor image processing based on a setting value set in advance relating to the image processing on image data generated by the endoscope by capturing an image of an inside of the subject;
accessing, by a controller, a recorder configured to record setting information as setting values for respective multiple sets of image processing, the setting values being determined according to a combination of:
at least one of identification information for identifying a type of the endoscope and observation light information about observation light that is emittable by a light source device that supplies the observation light to the endoscope for irradiating the inside of the subject; and
each of multiple modes,
wherein, for each combination of the identification information and the observation light information, the each of multiple modes is recorded in correspondence with the setting values for the respective multiple sets of image processing;
performing, by the controller, an acquisition of:
at least one of the identification information for identifying the endoscope connected to the processing device and the observation light information supplied by the light source device; and
information about one of the multiple modes selected by a user; and
setting, by the controller, the setting information specified based on a result of the acquisition as the setting values used in the image processing executed by the image processor;
receiving, by the controller, an instruction signal to change any one of the multiple modes and the setting values for the respective multiple sets of the image processing; and
in response to receiving the instruction signal to change any one of the setting values for the multiple sets of the image processing, collectively changing, by the controller, setting values for respective sets of image processing that are determined by a mode corresponding to a setting value to which the setting value is changed according to the instruction signal and, meanwhile, in response to receiving the instruction signal to make a change to any one of the multiple modes, collectively changing, by the controller, setting values for respective sets of image processing that are determined by the mode into which the mode is changed according to the instruction signal.

4. A non-transitory computer-readable recording medium on which an executable program is recorded, the executable program instructing one or more processors of a processing device to which an endoscope insertable into a subject is connected, to at least:
execute image processing based on a setting value set in advance relating to the image processing on image data generated by the endoscope by capturing an image of an inside of the subject;
access a recorder configured to record setting information as setting values for respective multiple sets of image processing, the setting values being determined according to a combination of:
at least one of identification information for identifying a type of the endoscope and observation light information about observation light that is emittable by a light source device that supplies the observation light to the endoscope for irradiating the inside of the subject; and
each of multiple modes,
wherein, for each combination of the identification information and the observation light information, the each of multiple modes is recorded in correspondence with the setting values for the respective multiple sets of image processing;
perform an acquisition of:
at least one of the identification information for identifying the endoscope connected to the processing device and the observation light information supplied by the light source device: and
information about one of the multiple modes selected by a user; and
set the setting information specified based on a result of the acquisition as the setting values used in the image processing executed by the image processor;
receive an instruction siqnal to change any one of the multiple modes and the setting values for the respective multiple sets of the image processing; and in response to receivinq the instruction siqnal to chanqe any one of the settinq values for the multiple sets of the imaqe processinq, collectively chanqe settinq values for respective sets of image processing that are determined by a mode corresponding to a setting value to which the setting value is changed according to the instruction signal and, meanwhile, in response to receiving the instruction signal to make a change to any one of the multiple modes, collectively change setting values for respective sets of image processing that are determined by the mode into which the mode is changed according to the instruction signal.

* * * * *